US012571923B2

(12) United States Patent
Poddar et al.

(10) Patent No.: US 12,571,923 B2
(45) Date of Patent: Mar. 10, 2026

(54) TIMER-BASED AMPLITUDE CORRECTION METHOD FOR PHOTON COUNTING COMPUTED TOMOGRAPHY

(71) Applicant: Analog Devices, Inc., Wilmington, MA (US)

(72) Inventors: Sunrita Poddar, Jamaica Plain, MA (US); Patrick S. Riehl, Lynnfield, MA (US); Matthew A. Woodruff, North Andover, MA (US)

(73) Assignee: Analog Devices, Inc., Wilmington, MA (US)

( * ) Notice: Subject to any disclaimer, the term of this patent is extended or adjusted under 35 U.S.C. 154(b) by 522 days.

(21) Appl. No.: 18/065,385

(22) Filed: Dec. 13, 2022

(65) Prior Publication Data

US 2024/0188918 A1 Jun. 13, 2024

(51) Int. Cl.
| | |
|---|---|
| *A61B 6/00* | (2024.01) |
| *G01R 29/027* | (2006.01) |
| *G01T 1/17* | (2006.01) |

(52) U.S. Cl.
CPC .......... *G01T 1/171* (2013.01); *G01R 29/0273* (2013.01); *A61B 6/5258* (2013.01); *A61B 2560/0223* (2013.01)

(58) Field of Classification Search
None
See application file for complete search history.

(56) References Cited

U.S. PATENT DOCUMENTS

| | | | |
|---|---|---|---|
| 7,180,074 | B1 | 2/2007 | Crosetto |
| 7,800,070 | B2 | 9/2010 | Weinberg et al. |
| 7,829,860 | B2 | 11/2010 | Nygard et al. |
| 7,863,578 | B2 | 1/2011 | Brenner et al. |
| 7,884,317 | B2 | 2/2011 | Casper |
| 8,384,038 | B2 | 2/2013 | Guo et al. |
| 8,941,076 | B2 | 1/2015 | Abraham |
| 9,176,238 | B2 | 11/2015 | Herrmann et al. |
| 9,268,035 | B2 | 2/2016 | Herrmann |

(Continued)

FOREIGN PATENT DOCUMENTS

| | | |
|---|---|---|
| CN | 103685991 B | 10/2017 |
| CN | 113661381 A | 11/2021 |

(Continued)

OTHER PUBLICATIONS

Gustavsson et al., *A High-Rate Energy-Resolving Photon-Counting ASIC for Spectral Computed Tomography*, © 2012 IEEE Transactions on Nuclear Science, 14 pages.

(Continued)

*Primary Examiner* — Hoon K Song

(74) *Attorney, Agent, or Firm* — ArentFox Schiff LLP

(57) ABSTRACT

One embodiment is a method of deconvolving overlapping first and second pulses in a photon-counting CT scanning system, the method comprising detecting a first pulse event having a first detected level; detecting a second pulse event having a second detected level; determining an amount of time that elapses between the detected first pulse event and the detected second pulse event; and reconstructing the first pulse and the second pulse using the first and second detected levels, the duration of time between the first and second pulse events, and a known pulse shape.

20 Claims, 13 Drawing Sheets

(56) References Cited

U.S. PATENT DOCUMENTS

| | | | |
|---|---|---|---|
| 9,645,260 | B2 | 5/2017 | Abraham et al. |
| 9,750,471 | B2 | 9/2017 | Schirra et al. |
| 9,759,822 | B2 | 9/2017 | Daerr et al. |
| 10,080,533 | B2 | 9/2018 | Roessl et al. |
| 10,162,066 | B2 | 12/2018 | Fu et al. |
| 10,768,318 | B2 | 9/2020 | Qiang et al. |
| 2005/0228291 | A1 | 10/2005 | Chance |
| 2006/0015290 | A1* | 1/2006 | Warburton ............... G01T 1/17 |
| | | | 702/178 |
| 2008/0025385 | A1 | 1/2008 | Barat et al. |
| 2010/0020924 | A1 | 1/2010 | Steadman Booker et al. |
| 2010/0181491 | A1 | 7/2010 | Karim et al. |
| 2012/0019946 | A1 | 1/2012 | Aravind |
| 2013/0229213 | A1 | 9/2013 | Park et al. |
| 2015/0063527 | A1 | 3/2015 | Daerr et al. |
| 2015/0185332 | A1* | 7/2015 | Herrmann ............. H03M 1/125 |
| | | | 250/336.1 |
| 2015/0327827 | A1 | 11/2015 | Teshigawara |
| 2016/0170039 | A1 | 6/2016 | Proksa |
| 2016/0377745 | A1 | 12/2016 | Daerr et al. |
| 2017/0205284 | A1 | 7/2017 | De Geronimo |
| 2020/0379133 | A1 | 12/2020 | Burr et al. |
| 2021/0239856 | A1 | 8/2021 | Sjolin |
| 2021/0382188 | A1 | 12/2021 | Steadman et al. |
| 2021/0401387 | A1* | 12/2021 | Hupfer ..................... G01T 1/17 |

FOREIGN PATENT DOCUMENTS

| | | |
|---|---|---|
| EP | 2049917 B1 | 4/2015 |
| EP | 3074791 B1 | 6/2019 |
| JP | S6021474 A | 2/1985 |
| JP | H07-508202 A | 9/1995 |
| JP | H11-510900 A | 9/1999 |
| JP | 2016-506504 A | 3/2016 |
| JP | 2016-506507 A | 3/2016 |
| JP | 2016-540208 A | 12/2016 |
| JP | 2016-540209 A | 12/2016 |
| KR | 10-2011-0113606 A | 10/2011 |
| WO | 2013093726 A1 | 6/2013 |
| WO | 2020208333 A1 | 10/2020 |

OTHER PUBLICATIONS

International Search Report and Written Opinion for International Patent Application No. PCT/US2023/079474, mailed on Feb. 20, 2024, 14 pages.

International Search Report and Written Opinion for International Patent Application No. PCT/US22/26453, mailed on Aug. 8, 2022, 7 pages.

Extended European Search Report received for European Patent Application No. 22808034.7, mailed on Sep. 24, 2024, 5 pages.

Kleczek et al., "The design of low power low noise high speed CMOS readout front-end electronics for silicon strip detectors", Mixed Design of Integrated Circuits and Systems (MIXDES), 2011 Proceedings of the 18th International Conference, IEEE, Jun. 16, 2011, pp. 374-378.

* cited by examiner

FIG. 5

PILEUP EXAMPLE

TIMER-BASED AMPLITUDE CORRECTION METHOD FOR PHOTON COUNTING COMPUTED TOMOGRAPHY

FIELD OF THE DISCLOSURE

This disclosure relates generally to the field of energy level event counters and, more particularly, to an energy bin event counting system that enables improved performance during pile-up scenarios.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 5 is a graph illustrating results of a simulation example of the photon-counting CT scanning system of FIG. 2 in which there are overlapping charge events using three different counting techniques in accordance with features of certain embodiments described herein;

DETAILED DESCRIPTION OF EXAMPLE EMBODIMENTS

Figure 1:
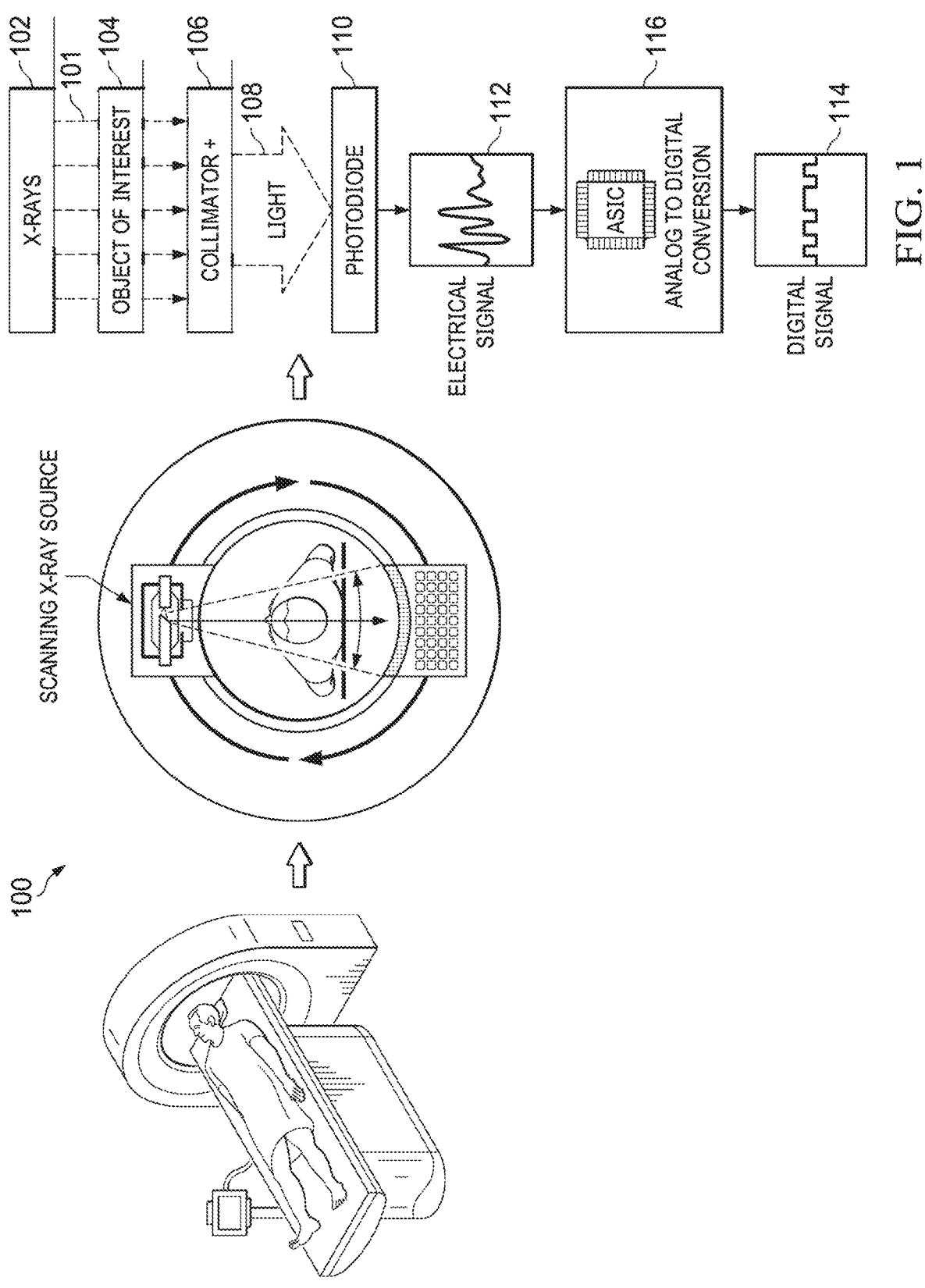
FIG. 1 is a schematic diagram illustration of operation of a conventional CT scanning system in accordance with features of certain embodiments described herein.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C). The term "between," when used with reference to measurement ranges, is inclusive of the ends of the measurement ranges. When used herein, the notation "A/B/C" means (A), (B), and/or (C).

The description uses the phrases "in an embodiment" or "in embodiments," which may each refer to one or more of the same or different embodiments. Furthermore, the terms "comprising," "including," "having," and the like, as used with respect to embodiments of the present disclosure, are synonymous. The disclosure may use perspective-based descriptions such as "above," "below," "top," "bottom," and "side"; such descriptions are used to facilitate the discussion and are not intended to restrict the application of disclosed embodiments. The accompanying drawings are not necessarily drawn to scale. Unless otherwise specified, the use of the ordinal adjectives "first," "second," and "third," etc., to describe a common object, merely indicate that different instances of like objects are being referred to and are not intended to imply that the objects so described must be in a given sequence, either temporally, spatially, in ranking or in any other manner.

In the following detailed description, reference is made to the accompanying drawings that form a part hereof, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense.

The following disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming, it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as "above", "below", "upper", "lower", "top", "bottom", or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase "between X and Y" represents a range that includes X and Y.

Further, the present disclosure may repeat reference numerals and/or letters in the various examples. This repetition is for the purpose of simplicity and clarity and does not in itself dictate a relationship between the various embodiments and/or configurations discussed. Example embodiments that may be used to implement the features and functionality of this disclosure will now be described with more particular reference to the accompanying FIGURES.

Referring to FIG. 1, a conventional computed tomography (CT) scanning system 100 employs X-rays 101 generated by an X-ray source 102 and passed through an object of interest 104. The X-rays are transformed by a collimator and scintillator 106 into light 108 that is captured by a detector implemented as photodiode arrays 110. The photodiode arrays 110 transform the light 108 into analog electrical signals 112, which are converted into digital signals 114 by an analog-to-digital (A/D) converter 116. The digital signals output from the A/D converter are used to produce a gray scale image referred to as a CT scan.

Photon-counting CT (PCCT) imaging is a newer technique that may offer significant advantages and improvements over existing CT imaging techniques described above. A PCCT system employs a photon-counting detector (PCD) comprising a semiconductor layer for implementing an array of detector pixels that register the interactions of individual photons with the PCD. By tracking the deposited energy of each interaction, detector pixels of a PCD record an approximate energy spectrum as well as intensity of the photons, such that PCCT is a spectral, or energy-resolved, CT technique. In contrast, traditional CT scanners use energy-integrating detectors (EIDs) in which the total energy from one or more photons as well as electronic noise deposited in a pixel during a fixed period of time is registered. EIDs therefore register only photon intensity, analogous to black-and-white photography. In contrast, PCDs register both photon intensity and spectral information, analogous to color photography.

PCCT imaging turns the multi-step process described above with reference to FIG. 1 into a more streamlined direct conversion from X-ray to charge via a semiconductor layer comprising the PCD. In particular, the semiconductor material used to implement the PCD efficiently turns each X-ray photon into a burst of charge that is proportional to the energy of the X-ray. Benefits of this technology include improved signal-to-noise, reduced X-ray dose to the patient due to the higher resolution that may be achieved with the same X-ray dose, improved spatial resolution and the ability to distinguish multiple contrast agents and multiple types of materials/tissues through use of several "energy bins".

When a photon interacts in a PCD, the height of a resulting electrical pulse is approximately proportional to the energy of the photon. By comparing each pulse produced in a pixel with a suitable low-energy threshold, contributions from low-energy events (resulting from both photon interactions and electronic noise) can be filtered out. As a result, PCDs have higher signal-to-noise and contrast-to-noise ratios as compared to EIDs, enabling an increase in image quality at the same X-ray exposure level or a decrease in patient X-ray dose with the same image quality.

Introduction of more energy thresholds above the low-energy threshold enables a PCD to be divided into several discrete energy bins. Each registered photon is assigned to a specific bin depending on its energy, such that each pixel measures a histogram of the incident X-ray spectrum. This spectral information enables a qualitative determination of the material composition of each pixel in the reconstructed CT image, as opposed to the estimated average linear attenuation coefficient obtained in a conventional CT scan. Additionally, using more than two energy bins enables discrimination between dense bones and calcifications versus heavier elements commonly used as contrast agents, reducing the need for a reference scan before contrast injection and thereby further reducing the amount of X-ray dose to which a patient is subjected.

Figure 2:
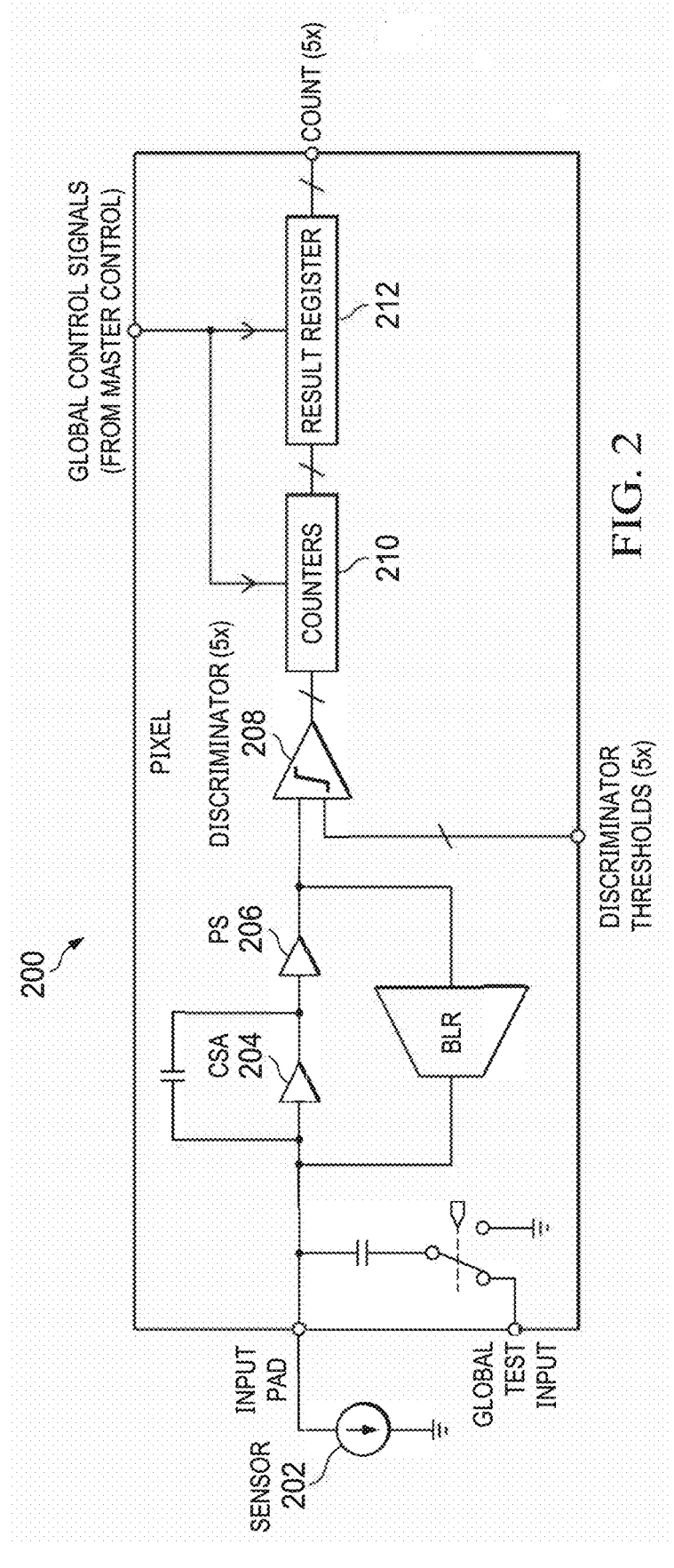
FIG. 2 is a schematic block diagram of a photon-counting CT scanning system in accordance with features of certain embodiments described herein.

FIG. 2 illustrates a schematic diagram of an example signal processing architecture for a photon-counting CT system 200 comprising a PCD including a plurality of detector pixels, represented in FIG. 2 by a single pixel. In operation, a pulse of current comes in from a sensor 202, is amplified by a charge-sensitive amplifier (CSA) 204 and shaped by a pulse shaper (PS) 206. The voltage pulse output from the PS 206 is input to a set of N discriminators (or comparators) 208, which respectively compare the pulse to N increasing voltage thresholds. The set of discriminators 208 create pulsed digital outputs in a "thermometer code." The pulses may be counted at each level, or threshold, by counters 210, with the resulting count values (which may be temporarily stored in result registers 212) representing how many X-ray hits at each of the N thresholds have occurred. It will be recognized that the thresholds are set to match the different voltages corresponding to the different energy photons.

PCCT detectors may experience pileup when the characteristic signals, or pulses, corresponding to two separate events overlap in time. Two such overlapping events may be mistakenly detected as a single event with higher energy, leading to errors in both the total number of events counted, as well as event energy spectrum detected. In theory, it may be possible to deconvolve the two signals to recover the actual energy of each of the two events; however, performing deconvolution using the simple detector electronics available within a PCCT pixel has proven far more difficult.

In accordance with features of embodiments described herein, deconvolution of overlapping events may be performed within a PCCT pixel in a manner in which a significant amount of lost information may be recovered. In particular, event signal pulses have a characteristic shape that is predictable; as a result, pileup events may be modeled as the sum of two or more such characteristic pulses. As will be described in detail below, using a few measurements describing the shape of a pulse resulting from a pileup evet, it is possible to identify the most likely combination of characteristic pulses that resulted in the pileup event. This allows information that would otherwise be lost to be recorded by the detector, in turn leading to better image quality in the PCCT scan.

As will be described in detail below, events may be detected in a variety of manners, including "tick down" and/or time-over-threshold (TOT) methods or techniques. Additionally, a time lapse between the detected event and an immediately preceding event is measured. Using this information, along with the shape of the detected event, known as a basis pulse or basis function, (which is repeatable), the sequence of actual events comprising the pileup event may be estimated. The system may be implemented as either a synchronous digital state machine, or an asynchronous state machine with timers.

Figure 3:
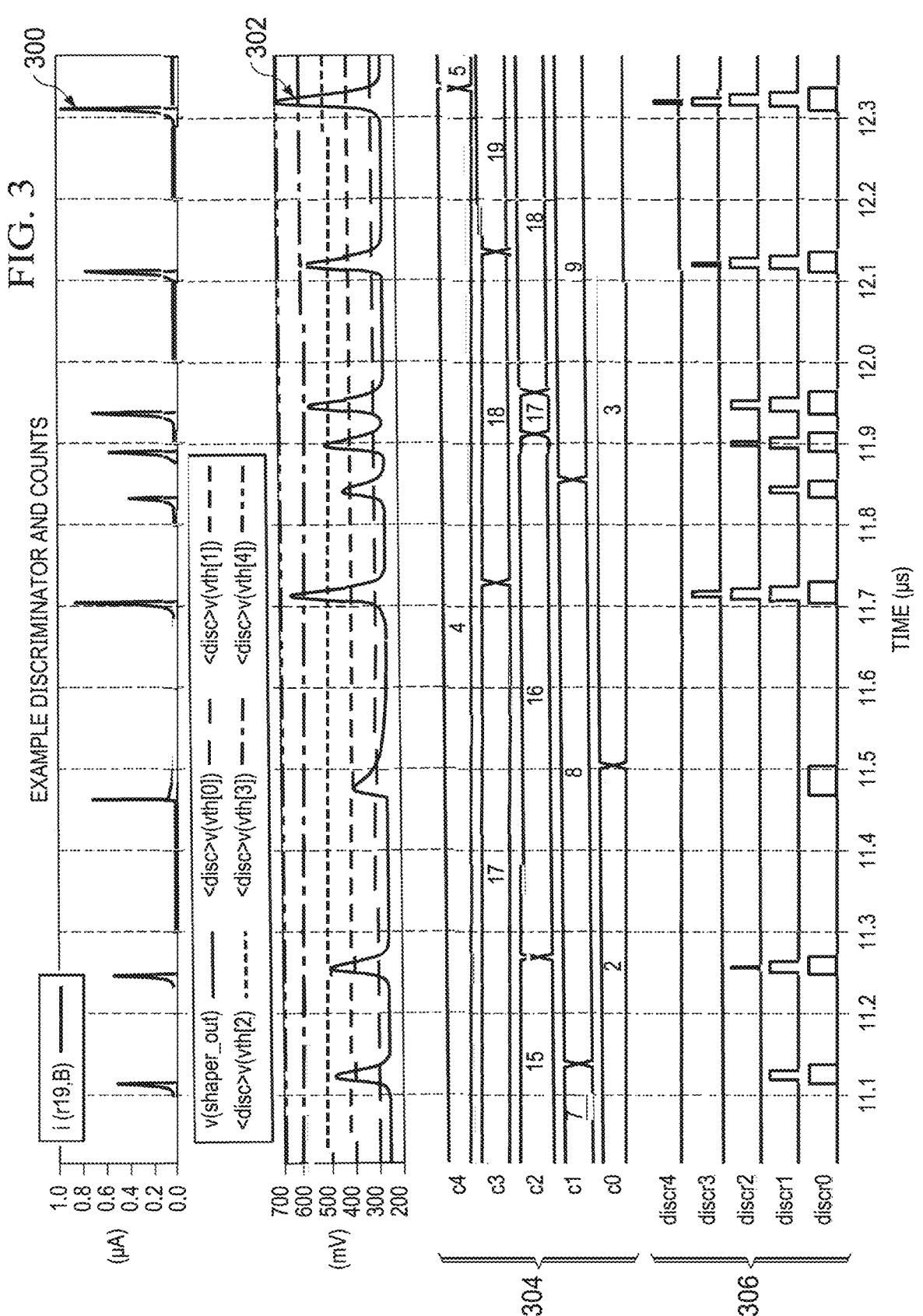
FIG. 3 is a graph illustrating results of a simulation example of the photon-counting CT scanning system of FIG. 2 in accordance with features of certain embodiments described herein.

FIG. 3 is a graph illustrating results of a simulation example of a photon-counting CT system illustrated in FIG. 2 in which there are no overlapping charge events. A first waveform 300 represents current pulses from the sensor 202 and a second waveform 302 represents corresponding voltage pulses output from the PS 206 vs. increasing voltage thresholds expressed in millivolts (mV). Waveforms 304 represent the corresponding pulses counted at each level by counters 210. Finally, waveforms 306 represent outputs of discriminators 208 input to counters 210. It will be noted from FIG. 3 that, for each pulse of current, a voltage pulse from the pulse shaper generates outputs on the discriminators 208. Counting by the counters 210 of the peak discriminator output for each pulse is the desired response.

When all of the pulses occur far enough apart in time, as illustrated in FIG. 3, there are multiple ways to effectively implement counters to count and "bin" the pulses. Two common techniques of doing so include asynchronous edge (asynch_edge) counting and peak zero (peak_zero) counting. Using asynchronous edge counting, an asynchronous counter is associated with each discriminator output. As a result, the counter increments for any energy level above the threshold level of the associated discriminator. If a "binned" value is required, for each counter, the counts of the higher threshold level counters must be subtracted from the count to determine the correct count for threshold level. For example, the counter associated with discriminator 0 is also incremented for every discriminator 1-N count; therefore, to get an accurate level 0 count, counts for discriminators 1-N must be subtracted from the count for discriminator 0. Similarly, the counter associated with discriminator 1 is also incremented for every discriminator 2-N count; therefore, to get an accurate level 1 count, counts for discriminators 2-N must be subtracted from the count for discriminator 1.

Using peak zero counting, the edges of the signals output from discriminator 0 are used to decide which counter to increment. The method is basically to increment only the maximum discriminators count that occurs between the rise and fall of discriminator 0.

Both asynchronous edge counting and peak zero counting work reasonably well when the events being counted are spaced apart without any overlap. If there are no other charge events, there will always be an orderly sequence starting and ending with discriminator 0 rising and falling. There will also be a rising edge of all levels below the maximum switching discriminator.

Figure 4:
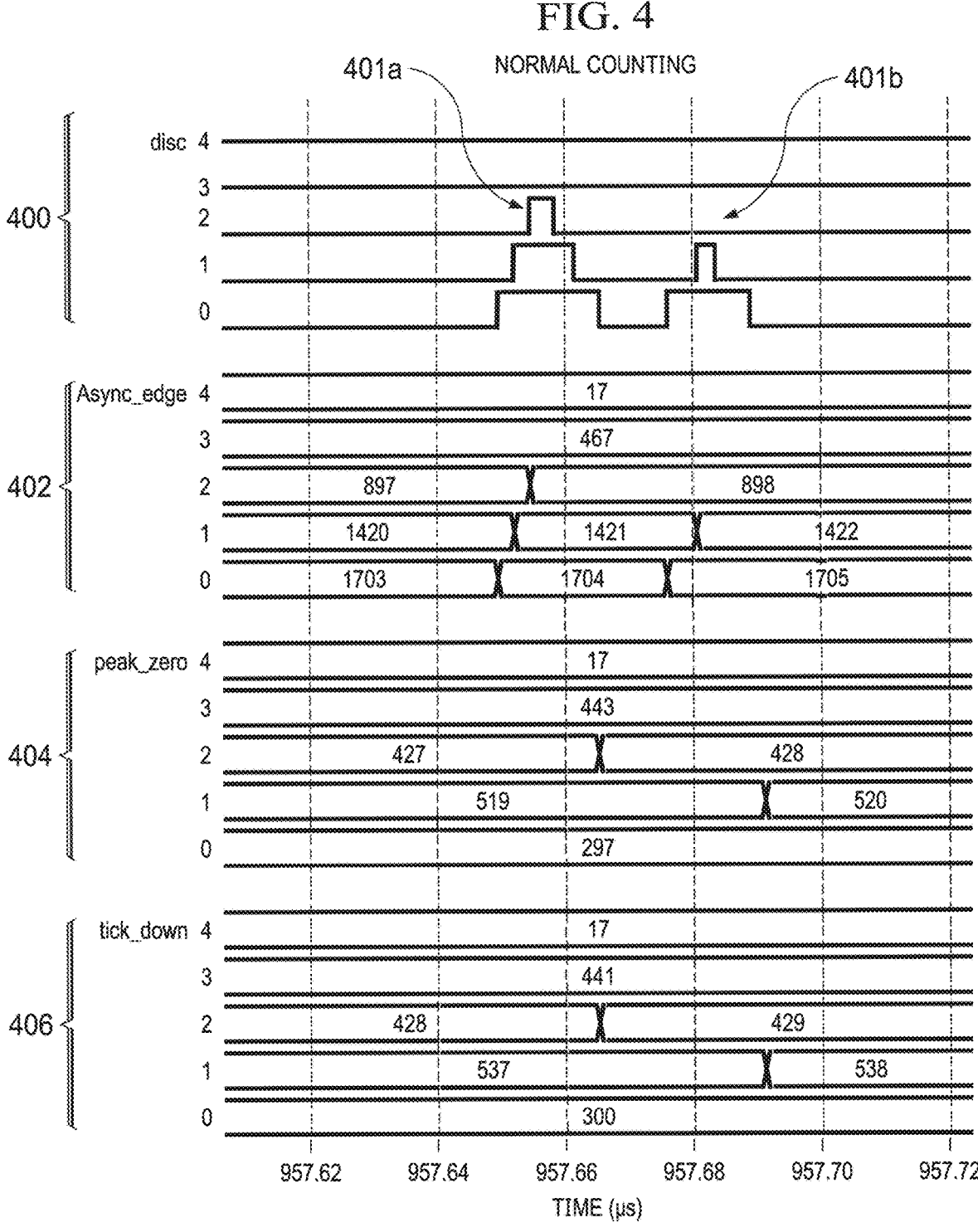
FIG. 4 is a graph illustrating results of a simulation example of the photon-counting CT scanning system of FIG. 2 in which there are no overlapping charge events using three different counting techniques in accordance with features of certain embodiments described herein.

FIG. 4 illustrates operation of asynchronous edge and peak zero counting in a case such as that described above in which the charge events are spaced apart with no overlap. Referring to FIG. 4, a set of waveforms 400 correspond to outputs of discriminators 0-4. As visible from waveform 400, there are two charge events 401a, 401b. A set of waveforms 402 illustrate cumulative count values for threshold levels 0-4 in response to the charge events 401a, 401b, using asynchronous edge counting to implement the counters. In contrast, as set of waveforms 404 illustrate cumulative count values for threshold levels 0-4 in response to the charge events 401a, 401b, when peak zero counting is used to implement the counters.

A set of waveforms 406 illustrate cumulative count values for threshold levels 0-4 in response to the charge events 401a, 401b, using a counting technique described herein and referred to as a "tick down" technique.

In the scenario illustrated in FIG. 4, which will be referred to herein as a "non-pile-up case," the asynchronous edge counters increment for each transition (requiring subtraction of count totals of higher threshold level counters from count totals of lower threshold level counters, as previously described) and the peak zero counters simply increment for the maximum level reached between levels. The tick down counters also increments only on the peak level reached; however, as will be described in greater detail with reference to FIG. 5, the tick down counters operate differently in situations in which there is a pile-up.

As previously noted, pile-up occurs when the charge events occur close enough together to disrupt the orderly transition up and down the discriminators. Pile-ups occur at higher rates as the X-ray flux increases and their rate can be predicted statistically. A pile-up situation is illustrated in FIG. 5.

Figure 5:
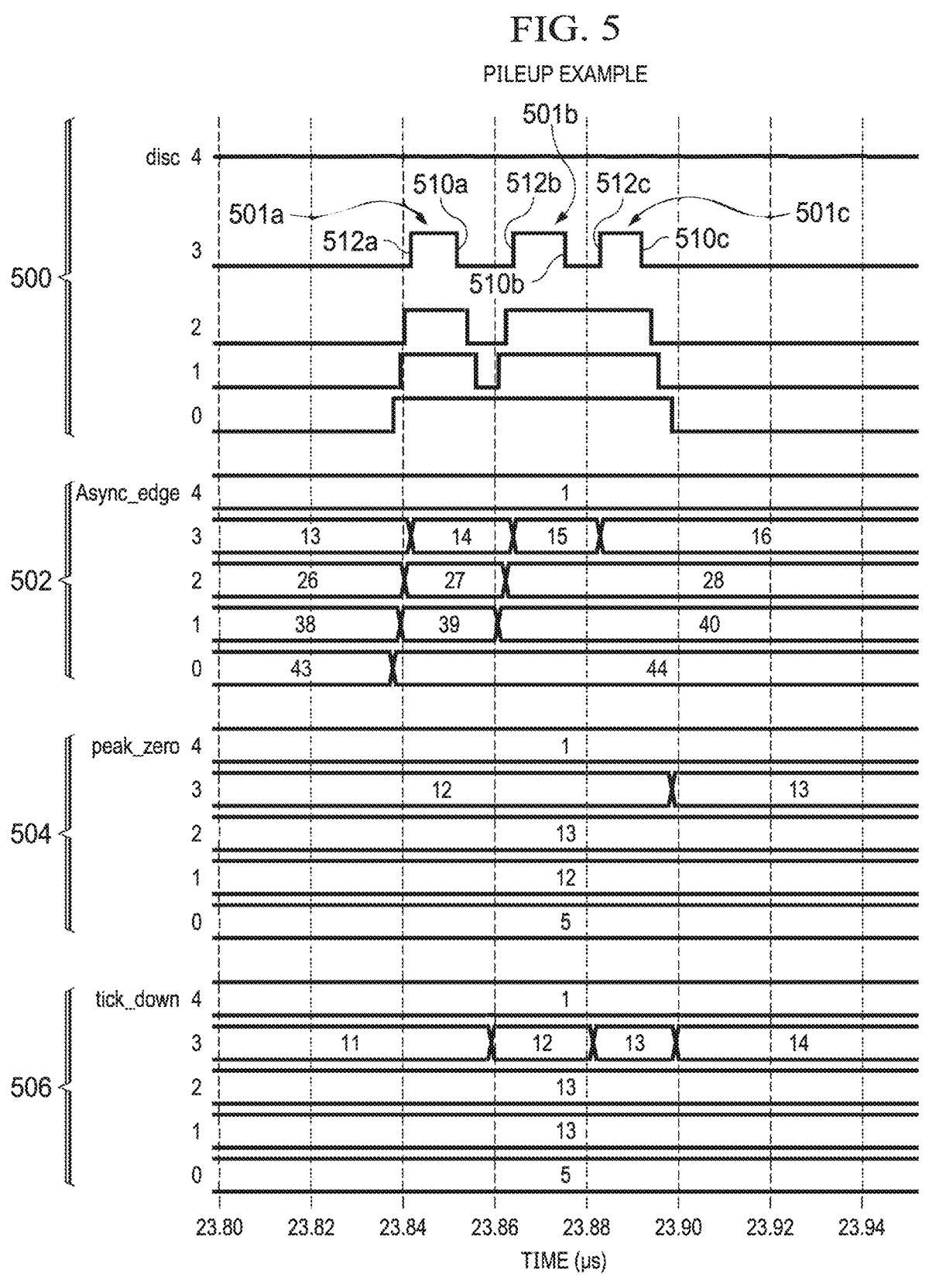

Referring to FIG. 5, a set of waveforms 500 correspond to outputs of discriminators 0-4. As visible from waveform 500, there are three charge events 501a-501c. Unlike the charge events 401a, 401b, shown in FIG. 4, the events 501a-501c are overlapping, creating a pile-up situation. A set of waveforms 502 illustrate cumulative count values for threshold levels 0-4 in response to the charge events 501a-501c, using asynchronous edge counting to implement the counters. In contrast, as set of waveforms 504 illustrate cumulative count values for threshold levels 0-4 in response to the charge events 501a-501c, when peak zero counting is used to implement the counters.

As illustrated in FIG. 5, the asynchronous edge counting technique fails to increment discriminator 0 for two of the three charge events, as would occur if the events were spread out as in FIG. 4. As also illustrated in FIG. 5, the peak zero counting technique fails to increment discriminator 3 for two of the three charge events 501a-501c, as would occur if the events were spread out as in FIG. 4, because it becomes paralyzed by failure of the energy level to fall back to the threshold level for discriminator 0. As illustrated by a set of waveforms 506, the tick down counting technique accurately counts all three charge events 501a-501c as discriminator 3 counts.

The tick down counting technique operates by identifying the peaks of discriminator outputs by only counting "downtick" events that are immediately preceded by an "up-tick" event. Referring again to FIG. 5, each down-tick 510a-510c of discriminator 3 is immediately preceded by a respective up-tick 512a-512c; therefore, the count for threshold level 3 is incremented three times (from 11 to 14). The various other down-ticks of the other discriminators are immediately preceded by down-ticks, rather than up-ticks, and are therefore not counted in the corresponding counter value.

It will be recognized that, while embodiments herein are described using a tick down counting technique, circuitry could be designed such to implement a tick up counting technique, in which only those up-ticks that are immediately followed by down-ticks are counted by the corresponding threshold level counter without departing from the spirit or scope of embodiments described herein.

Figure 6:
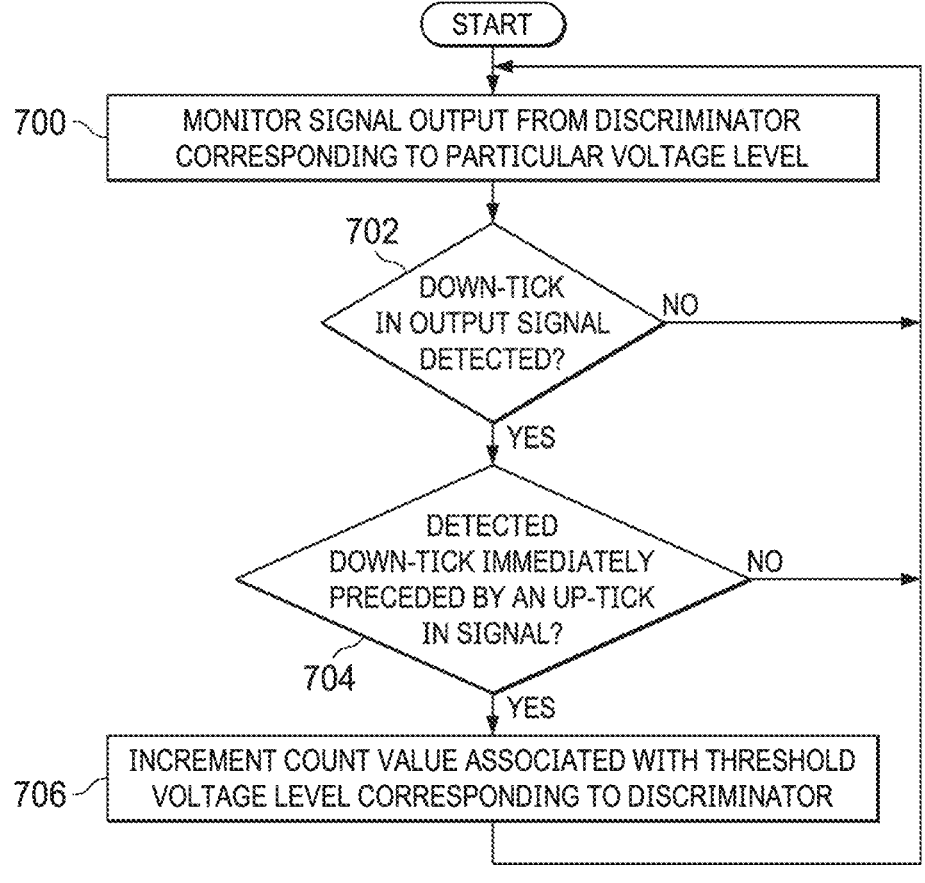
FIG. 6 is a flow chart illustrating example operation of a photon-counting CT scanning system in accordance with a tick-down counting method described herein.

FIG. 6 is a flow chart illustrating example operation of a photon-counting CT scanning system using a tick-down method referred to above. It will be noted that the steps shown in FIG. 6 may be implemented in connection with each discriminator/counter combination corresponding to a particular threshold voltage level as described above. Referring to FIG. 6, in step 700, the signal output from the discriminator (which discriminator corresponds to a particular threshold voltage level) is monitored. In step 702, a determination is made whether a down-tick in the discriminator output signal is detected. If a negative determination is made in step 702, execution returns to step 700. Conversely, if a positive determination is made in step 702, execution proceeds to step 704.

In step 704, a determination is made whether the downtick detected in step 702 was immediately preceded in the output signal by an up-tick. If a negative determination is made in step 704, execution returns to step 700. Conversely, if a positive determination is made in step 704, execution proceeds to step 706. In step 706, the count value (e.g., a counter register) associated with the threshold voltage level of the discriminator is incremented by one.

Figure 7:
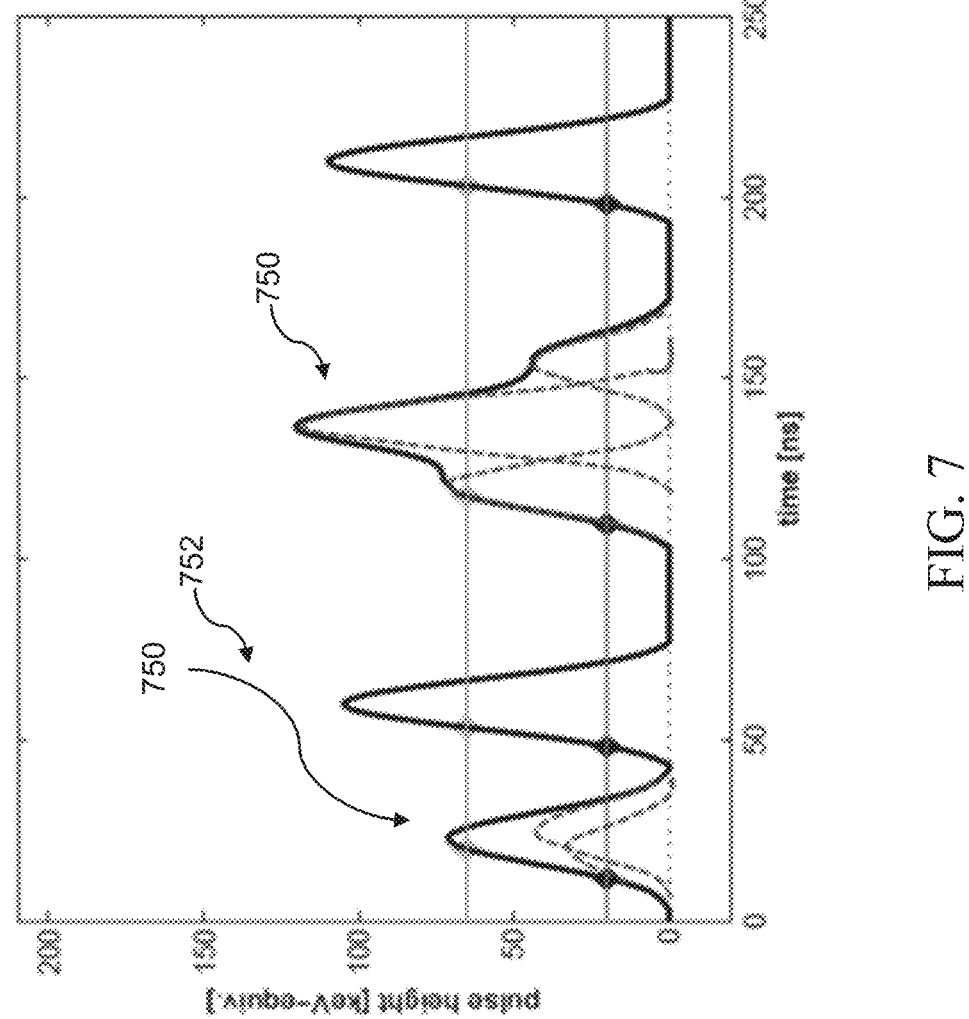
FIG. 7 is a graph illustrating examples of pileups in accordance with features of embodiments described herein.

As previously noted, photon counting detectors experience pulse pileup when two events occur too close together in time for the detector to be able to distinguish the pulses from one another. FIG. 7 is a graph illustrating several such pulse pileup events 750. It will be recognized that pulses have a characteristic shape that is predictable, such that pileup events can be modeled as a sum of two or more such characteristic pulses, such as characteristic pulse 752. With a few measurements describing the shape of the pulse resulting from a pileup event, it is possible to identify the most likely combination of characteristic pulses that resulted in the pileup event. As a result, information that would otherwise be lost may be recovered by the detector, which in turn leads to better image quality in the CT scan.

Figure 8:
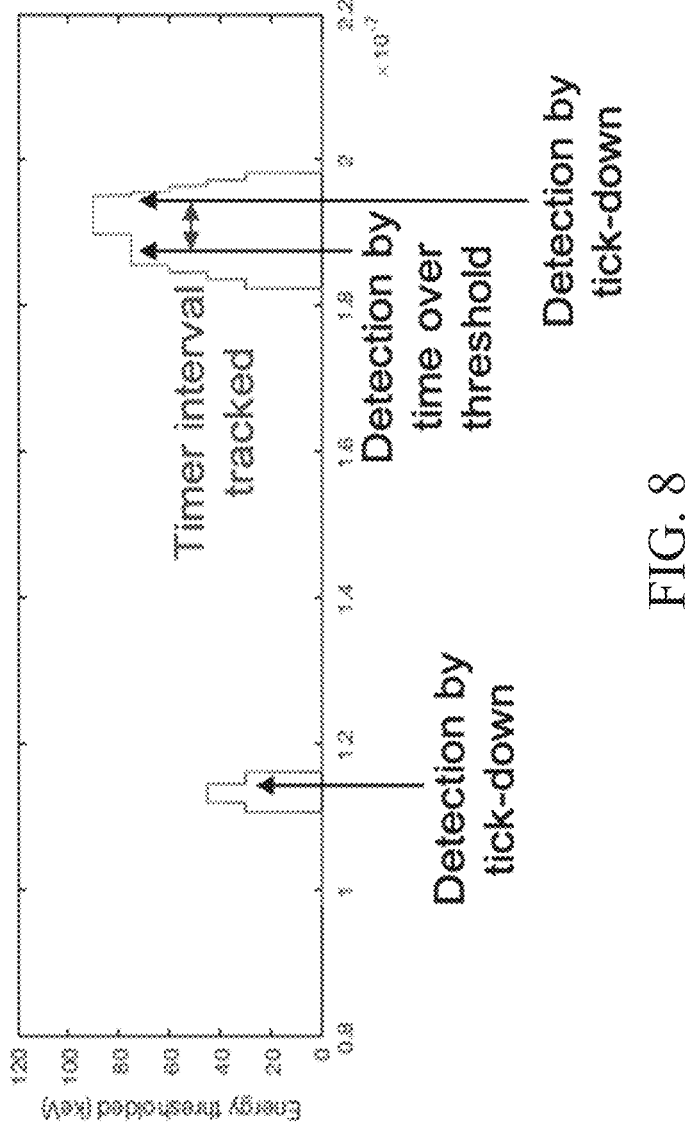
FIG. 8 is a graph illustrating various pulse detection mechanisms used to implement a Timer-Based Amplitude Correction (TBAC) technique in accordance with embodiments described herein.

As illustrated in FIG. 8, in accordance with features of embodiments described herein, a TBAC method tracks the time elapsed between pulse detections and accordingly compensates for the energy level distortions due to pulse pileup. Pulse detections can occur using a time-over-threshold (TOT) event, in which a threshold time elapses between two threshold crossings, and/or a tick-down event, in which a threshold is crossed in the negative direction immediately after the same threshold is crossed in the positive direction. The TBAC method makes use of a single timer that raises an alarm in response to crossing a specified threshold T ns. In accordance with features of embodiments described herein, the first two pulses in a pileup are jointly estimated. For the third and subsequent pulses, only the tail of the previous pulse is compensated for.

Corrected pulse amplitudes $A_1$ and $A_2$ may be estimated using the following equations:

$$A_1 = (L_1 - L_2 * p(-\tau))/(1 - p(-\tau)(p(\tau)))$$

$$A_2 = (L_2 - L_1 * p(\tau))/(1 - p(-\tau)(p(\tau)))$$

where:
  $p(\tau)$ is known pulse shape;
  $L_1$ and $L_2$ are detected levels; and
  $\tau$ is elapsed time.

Figure 9A:
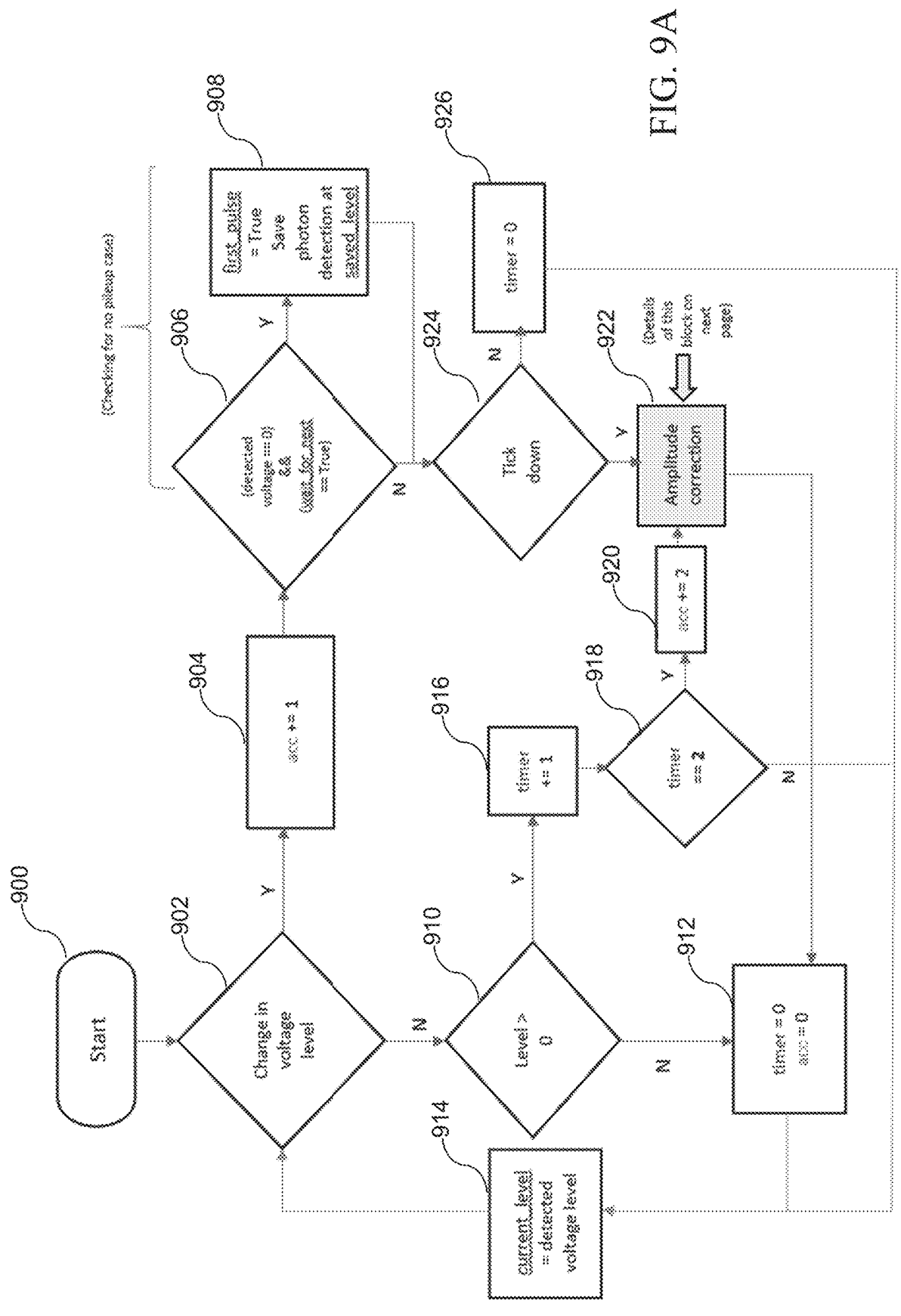
FIG. 9A is a flowchart illustrating example operations of a synchronous TABC technique in accordance with embodiments described herein.
Figure 9B:
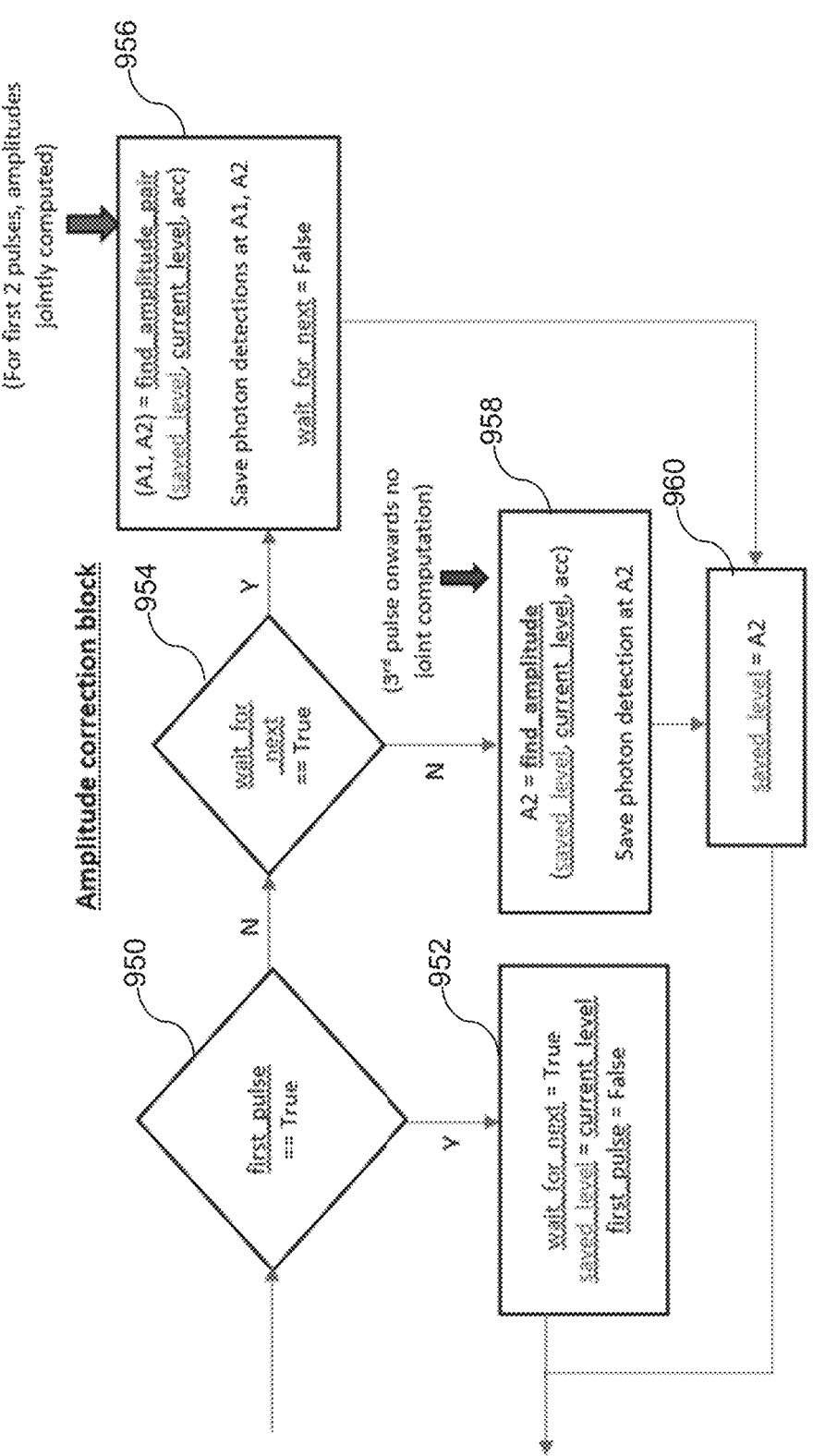
FIG. 9B is a flowchart illustrating example operations of a method of amplitude correction in accordance with embodiments described herein.

FIGS. 9A and 9B are flowcharts illustrating example operation of the TBAC method for use in a clocked system in accordance with embodiments. As illustrated in FIGS. 9A and 9B, at each new level, a determination is made whether a timer has exceeded a threshold amount of time T ns. The timer may be reset when (1) a new level is encountered or (2) a (TOT) event occurs. The number of level changes that occur between pulse detection are tracked as a proxy for the time elapsed between detections. If no (TOT) event occurs, each level change is approximated as a T/2 ns time elapse. Occurrence of a (TOT) event accounts for a T ns time elapse. When a pulse is detected, the estimated time elapse from the last detection is used to compensate for contributions from the previous pulse and the counter that was tracking the number of level changes is reset to zero. Initial values are set as follows:
  timer=0
  acc=0
  wait_for_next=False
  first_pulse=True
  saved_level=0
  current_level=0

Figure 9C:
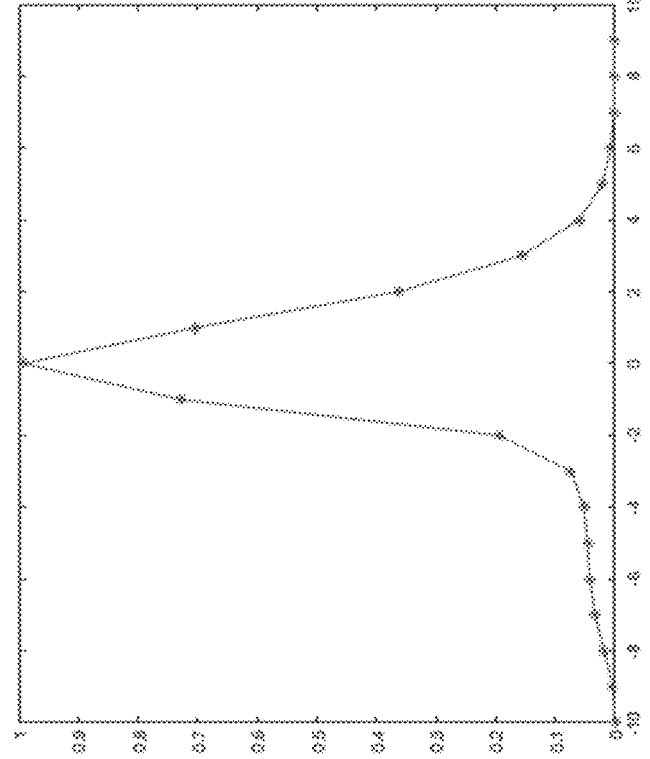
FIG. 9C is a graph illustrating a template of a characteristic pulse in accordance with embodiments described herein.

Amplitudes are computed based on first event amplitude, second event amplitude, number of samples between two events, and a template of characteristic pulse shape (FIG. 9C).

Referring again to FIG. 9A, execution begins at 900. At 902, a determination is made whether a change in voltage level has been detected. If so, execution proceeds to 904, at which the value of acc is incremented by 1, and then to 906, at which a determination is made whether the detected voltage is equal to 0 and wait_for_next is equal to True. If at 906 the detected voltage is equal to 0 and wait_for_next is equal to True, execution proceeds to 908. At 908, first_pulse is set to True and the photon detection is saved as saved_level. In particular, before 908 is reached, amplitude correction at 922 (described below) would have been performed at least once, since any event must involve at least one tick up and at least one tick down in voltage level. Saved_level is stored during this subroutine.

If at 902, it is determined that a change in voltage level has not been detected, execution proceeds to 910, at which a determination is made whether the detected voltage level is greater than 0. If the detected voltage level is not greater than 0, execution proceeds to 912, at which both the timer value and the acc value are reset to 0, and then to 914, at which current_level is set to the detected voltage level. Execution then returns to 902.

If at 910 it is determined that the detected voltage level is greater than 0, execution proceeds to 916, at which the value of timer is incremented by 1. At 918, a determination is made whether the value of timer is equal to 2. If not, execution proceeds to 914; otherwise, execution proceeds to 920. At 920, the value of acc is incremented by 2 and execution proceeds to 922. At 922, an amplitude correction process (shown in and described below with reference to FIG. 9B) is performed. Once the amplitude correction process has been completed, execution proceeds to 912. At 912, the values of timer and acc are reset to 0 and execution proceeds to 914. At 914 current_level is set to the detected voltage level. Execution then returns to 902.

If at 906 the detected voltage is not equal to 0 and/or wait_for_next is not equal to True, execution proceeds to 924. Similarly, after execution of 908, execution proceeds to 924. At 924, a determination is made whether a tick down has been detected. If so, execution proceeds to step 922, at which the amplitude correction process is performed; otherwise, execution proceeds to 926. At 926, the value of time is reset to 0 and execution proceeds to 914. At 914, current_level is set to the detected voltage level and execution returns to 902.

Referring now to FIG. 9B, illustrated therein is an amplitude correction process executed at 922 of the flowchart shown in FIG. 9A. At 950, a determination is made whether first_pulse is equal to True. If it is determined that first_pulse is equal to True, execution proceeds to 952, at which wait_for_next is set to True, saved_level is set to current_level, and first_pulse is set to False. At 954, a determination is made whether wait_for_next is equal to True. If it is determined that wait_for_next is equal to True, at 956, the amplitudes of the first two pulses (A1 and A2) are jointly computed and photon detections are saved at A1 and A2. Wait_for_next is then set to False.

The goal of the TBAC algorithm is to reconstruct the sequence of events that caused the observed pattern of discriminator codes. If the discriminator output were high-fidelity, the algorithm would approximate something like a wavelet transform using a basis function that corresponds to the known pulse shape. In practice, the discriminator output is heavily quantized in both voltage and time, but the principle is the same. An equation can be written that superimposes two pulses of known shape and known amplitude that overlap in time to form a sequence of discriminator codes. Similarly, that equation can be inverted to solve for the most likely combination of two pulses that could cause a certain pattern of discriminator codes. The inverted equation can be implemented using mathematical operations or a lookup table, or any suitable method.

In this example, the amplitude estimation function models each pileup event as the superposition of two basis pulses. The shape of a basis pulse can be determined from the properties of the X-ray sensor and the amplifying circuitry. An example basis pulse is shown in FIG. 9C.

In this example, once two events are detected, the amplitudes of the first two events are computed in state 956.

Example pseudo-code for joint estimation of two amplitudes A1 and A2 is as follows:

function [$A1$,$A2$]=find_amplitude_pair($L1$,$L2$,$n$)

$L1$+=delta $L2$+=delta $p1$=template($n$)

$p2$=template($-n$)

fact=$1-p1*p2$ $A1$=threshold(($L1-L2*p2$)/fact)

$A2$=threshold(($L2-L1*p1$)/fact)

end

In this example, in a sequence consisting of more than two pulses, after the first two amplitudes are computed, the algorithm computes the amplitude of each new event as it is detected. The variable wait_for_next indicates whether the current event being processed is exactly the second event in a sequence. If is determined at 954 that wait_for_next is not equal to true, meaning that the event being processed is at least the 3rd in a sequence, at 958, a single amplitude (A2) is computed.

Example pseudo-code for estimation of a single amplitude is as follows:

function $A2$=find_amplitude($L1$,$L2$,$n$)

$L1$+=delta $L2$+=delta $p2$=template($n$)

$A2$=threshold($L2-L1*p2$)

end

Upon completion of amplitude computation in 956 or 958, execution proceeds to 960, at which saved_level is set to A2.

Although this embodiment models each pileup event as the superposition of two basis pulses, it should be obvious to a person having ordinary skill in the art that this method could be extended to model each pileup event as the superposition of 3 or more basis pulses.

Figure 10:
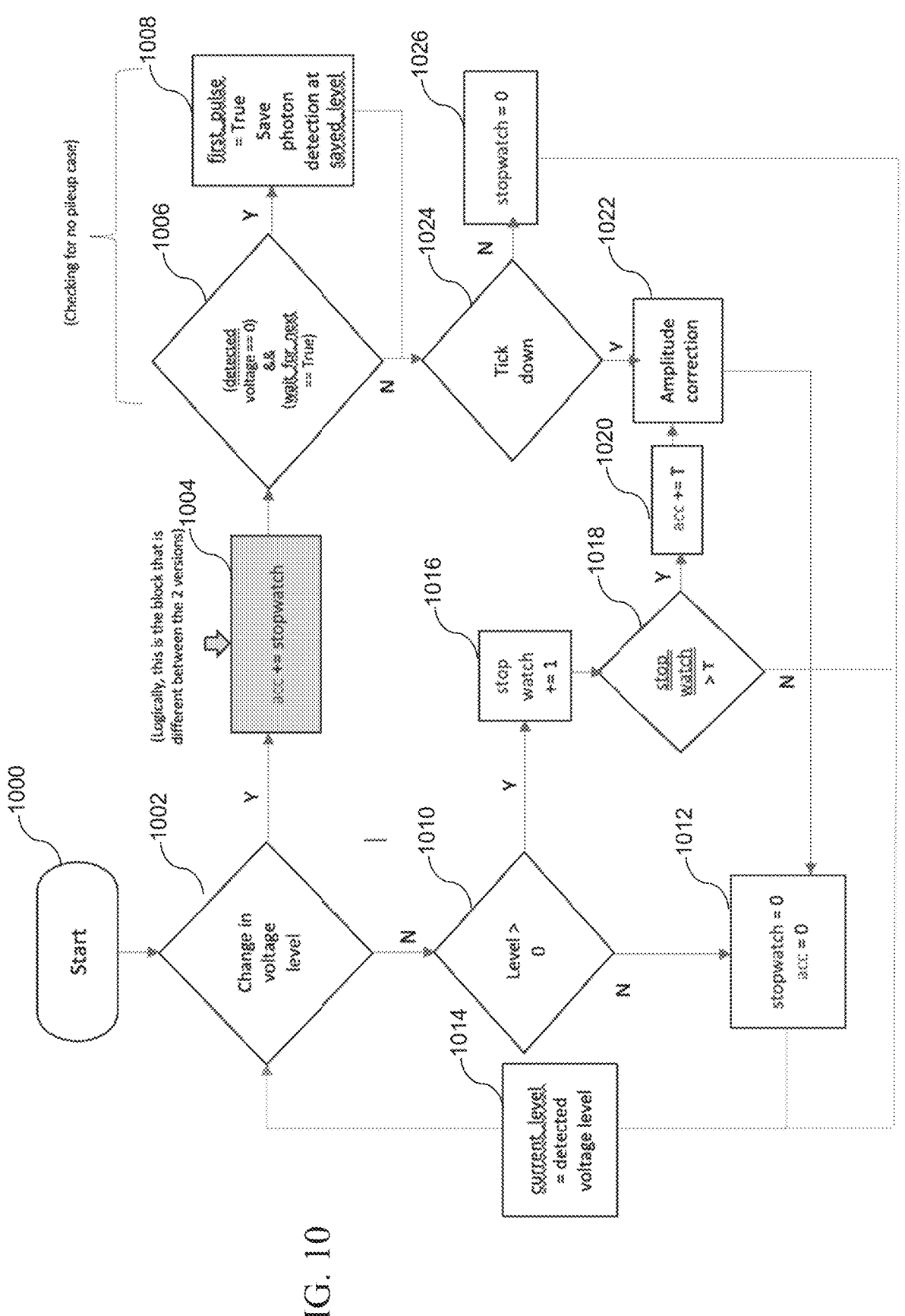
FIG. 10 is a flowchart illustrating example operations of an asynchronous TABC technique in accordance with embodiments described herein.

FIG. 10 is a flowchart illustrating example operation of the TBAC method for use in an asynchronous system in accordance with embodiments. As shown in FIG. 10, at each new level, a determination is made whether a stopwatch has exceeded a threshold amount of time T ns. The stopwatch may be reset when (1) a new level is encountered or (2) a (TOT) event occurs. The time that elapses between pulse detections is tracked using an accumulator and serves When a pulse is detected, the time elapsed from the last detection is used to compensate for contributions from a previous pulse. Initial values are set as follows:

stopwatch=0
    acc=0
    wait_for_next=False
    first_pulse=True

Referring again to FIG. 10, execution begins at 1000. At 1002, a determination is made whether a change in voltage level has been detected. If so, execution proceeds to 1004, at which the value of acc is incremented by the value of stopwatch, and then to 1006, at which a determination is made whether the detected voltage is equal to 0 and wait_for_next is equal to True. If at 1006 the detected voltage is equal to 0 and wait_for_next is equal to True, execution proceeds to 1008. At 1008, first_pulse is set to True and the photon detection is saved as saved_level.

If at 1002, it is determined that a change in voltage level has not been detected, execution proceeds to 1010, at which a determination is made whether the detected voltage level is greater than 0. If the detected voltage level is not greater than 0, execution proceeds to 1012, at which both the stopwatch value and the acc value are reset to 0, and then to 1014, at which current_level is set to the detected voltage level. Execution then returns to 1002.

If at 1010 it is determined that the detected voltage level is greater than 0, execution proceeds to 1016, at which the value of stopwatch is incremented by 1. At 1018, a determination is made whether the value of stopwatch is equal to 2. If not, execution proceeds to 1014; otherwise, execution proceeds to 1020. At 1020, the value of acc is incremented by 2 and execution proceeds to 1022. At 1022, an amplitude correction process (shown in and described above with reference to FIG. 9B) is performed. Once the amplitude correction process has been completed, execution proceeds to 1012. At 1012, the values of stopwatch and acc are reset to 0 and execution proceeds to 1014. At 1014 current_level is set to the detected voltage level. Execution then returns to 1002.

If at 1006 the detected voltage is not equal to 0 and/or wait_for_next is not equal to True, execution proceeds to 1024. Similarly, after execution of 1008, execution proceeds to 1024. At 1024, a determination is made whether a tick down has been detected. If so, execution proceeds to step 1022, at which the amplitude correction process is performed; otherwise, execution proceeds to 1026. At 1026, the value of time is reset to 0 and execution proceeds to 1014. At 1014, current_level is set to the detected voltage level and execution returns to 1002.

Figure 11:
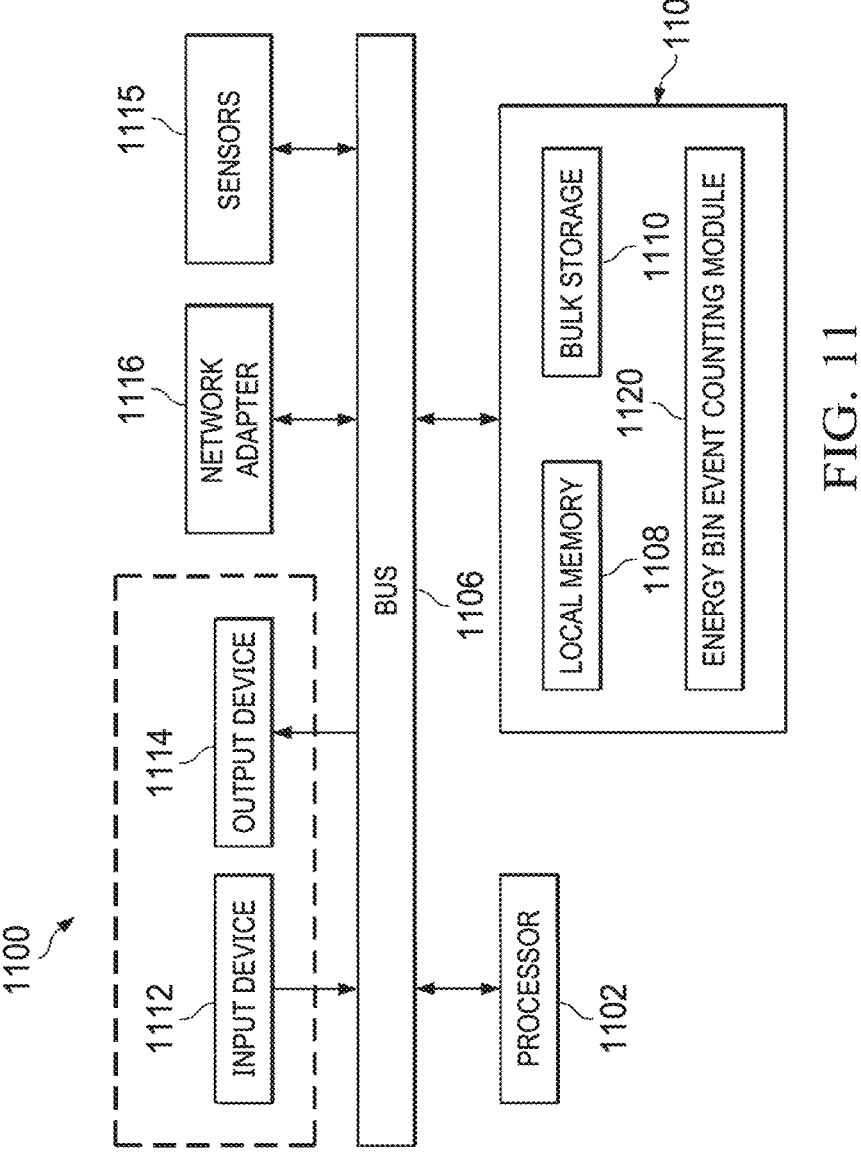
FIG. 11 is a block diagram of a computer system that may be used to implement all or some portion of a photon-counting CT scanning system in accordance with features of certain embodiments described herein.

FIG. 11 is a block diagram illustrating an example system 1100 that may be configured to implement at least portions of techniques in accordance with embodiments described herein, and more particularly as shown in the FIGURES described hereinabove. As shown in FIG. 11, the system 1100 may include at least one processor 1102, e.g., a hardware processor 1102, coupled to memory elements 1104 through a system bus 1106. As such, the system may store program code and/or data within memory elements 1104. Further, the processor 1102 may execute the program code accessed from the memory elements 1104 via a system bus 1106. In one aspect, the system may be implemented as a computer that is suitable for storing and/or executing program code. It should be appreciated, however, that the system 1100 may be implemented in the form of any system including a processor and a memory that is capable of performing the functions described in this disclosure.

In some embodiments, the processor 1102 can execute software or an algorithm to perform the activities as discussed in this specification; in particular, activities related to embodiments described herein. The processor 1102 may include any combination of hardware, software, or firmware providing programmable logic, including by way of nonlimiting example a microprocessor, a DSP, a field-programmable gate array (FPGA), a programmable logic array (PLA), an integrated circuit (IC), an application specific IC (ASIC), or a virtual machine processor. The processor 1102 may be communicatively coupled to the memory element 1104, for example in a direct-memory access (DMA) configuration, so that the processor 1102 may read from or write to the memory elements 1104.

In general, the memory elements 1104 may include any suitable volatile or non-volatile memory technology, including double data rate (DDR) random access memory (RAM), synchronous RAM (SRAM), dynamic RAM (DRAM), flash, read-only memory (ROM), optical media, virtual memory regions, magnetic or tape memory, or any other suitable technology. Unless specified otherwise, any of the memory elements discussed herein should be construed as being encompassed within the broad term "memory." The information being measured, processed, tracked or sent to or from any of the components of the system 1100 could be provided in any database, register, control list, cache, or storage structure, all of which can be referenced at any suitable timeframe. Any such storage options may be included within the broad term "memory" as used herein. Similarly, any of the potential processing elements, modules, and machines described herein should be construed as being encompassed within the broad term "processor." Each of the elements shown in the present figures may also include suitable interfaces for receiving, transmitting, and/or otherwise communicating data or information in a network environment so that they can communicate with, for example, a system having hardware similar or identical to another one of these elements.

In certain example implementations, mechanisms for implementing embodiments as outlined herein may be implemented by logic encoded in one or more tangible media, which may be inclusive of non-transitory media, e.g., embedded logic provided in an ASIC, in DSP instructions, software (potentially inclusive of object code and source code) to be executed by a processor, or other similar machine, etc. In some of these instances, memory elements, such as e.g., the memory elements 1104 shown in FIG. 11 can store data or information used for the operations described herein. This includes the memory elements being able to store software, logic, code, or processor instructions that are executed to carry out the activities described herein. A processor can execute any type of instructions associated with the data or information to achieve the operations detailed herein. In one example, the processors, such as e.g., the processor 1102 shown in FIG. 11, could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., an FPGA, a DSP, an erasable programmable read-only memory (EPROM), an electrically erasable programmable read-only memory (EEPROM)) or an ASIC that includes digital logic, software, code, electronic instructions, or any suitable combination thereof.

The memory elements 1104 may include one or more physical memory devices such as, for example, local memory 1108 and one or more bulk storage devices 1110. The local memory may refer to RAM or other non-persistent memory device(s) generally used during actual execution of the program code. A bulk storage device may be implemented as a hard drive or other persistent data storage device. The processing system 1100 may also include one or more cache memories (not shown) that provide temporary storage of at least some program code in order to reduce the number of times program code must be retrieved from the bulk storage device 1110 during execution.

As shown in FIG. 11, the memory elements 1104 may store an energy bin event counting module 1120. In various embodiments, the module 1120 may be stored in the local memory 1108, the one or more bulk storage devices 1110, or apart from the local memory and the bulk storage devices. It should be appreciated that the system 1100 may further execute an operating system (not shown in FIG. 11) that can facilitate execution of the module 1120. The module 1120, being implemented in the form of executable program code and/or data, can be read from, written to, and/or executed by the system 1100, e.g., by the processor 1102. Responsive to reading from, writing to, and/or executing the module 1120, the system 1100 may be configured to perform one or more operations or method steps described herein.

Input/output (I/O) devices depicted as an input device 1112 and an output device 1114, optionally, may be coupled to the system. Examples of input devices may include, but are not limited to, a keyboard, a pointing device such as a mouse, or the like. Examples of output devices may include, but are not limited to, a monitor or a display, speakers, or the like. In some implementations, the system may include a device driver (not shown) for the output device 1114. Input and/or output devices 1112, 1114 may be coupled to the system 1100 either directly or through intervening I/O controllers. Additionally, sensors 1115, may be coupled to the system 1100 either directly or through intervening controllers and/or drivers.

In an embodiment, the input and the output devices may be implemented as a combined input/output device (illustrated in FIG. 11 with a dashed line surrounding the input device 1112 and the output device 1114). An example of such a combined device is a touch sensitive display, also sometimes referred to as a "touch screen display" or simply "touch screen". In such an embodiment, input to the device may be provided by a movement of a physical object, such as e.g., a stylus or a finger of a user, on or near the touch screen display.

A network adapter 1116 may also, optionally, be coupled to the system 1100 to enable it to become coupled to other systems, computer systems, remote network devices, and/or remote storage devices through intervening private or public networks. The network adapter may comprise a data receiver for receiving data that is transmitted by said systems, devices and/or networks to the system 1100, and a data transmitter for transmitting data from the system 1100 to said systems, devices and/or networks. Modems, cable modems, and Ethernet cards are examples of different types of network adapter that may be used with the system 1100.

Example 1 provides a method of deconvolving overlapping pulses in a photon-counting CT scanning system, the method comprising detecting a number of events in a sequence of discriminator codes; determining amounts of time that elapsed between successive ones of the detected events; and reconstructing a most likely sequence of events that caused a measured pattern of discriminator codes based on measured code values associated with each of the detected events, the amounts of time that elapsed between successive ones of the detected events, and a known basis pulse shape.

Example 2 provides the method of example 1, wherein the reconstructing is performed using an arithmetic equation.

Example 3 provides the method of example 1, wherein the reconstructing is performed using a lookup table.

Example 4 provides the method of example 1, wherein the reconstructing is performed using a synchronous digital state machine.

Example 5 provides the method of example 1, wherein the reconstructing is performed using timers and an event-driven state machine.

Example 6 provides a method of deconvolving overlapping first and second pulses in a photon-counting CT scanning system, the method comprising detecting a first pulse event having a first detected level; detecting a second pulse event having a second detected level; determining an amount of time that elapses between the detected first pulse event and the detected second pulse event; and reconstructing the first pulse and the second pulse using the first and second detected levels, the duration of time between the first and second pulse events, and a known basis pulse shape.

Example 7 provides the method of example 6, wherein the detecting the first pulse event is performed using one of a time-over-threshold (TOT) event detection technique and a tick-down event detection technique.

Example 8 provides the method of example 6, wherein the detecting the second pulse event is performed using one of a time-over-threshold (TOT) event detection technique and a tick-down event technique.

Example 9 provides the method of example 6, further comprising incrementing a counter corresponding to the reconstructed first pulse.

Example 10 provides the method of example 6, further comprising incrementing a counter corresponding to the reconstructed second pulse.

Example 11 provides the method of example 6, wherein the reconstructing comprises performing an amplitude correction technique on the first and second pulses.

Example 12 provides the method of example 6, wherein the determining an amount of time that elapses between the detected first pulse event and the detected second pulse event comprises tracking a number of level changes that occur between the detection of the first pulse event and the detection of the second pulse event.

Example 13 provides the method of example 12, wherein the determining an amount of time that elapses between the detected first pulse event and the detected second pulse event further comprises, if a (TOT) event does not occur, approximating each of the level changes as an elapse of a threshold amount of time T ns divided by 2.

Example 14 provides the method of example 12, wherein the determining an amount of time that elapses between the detected first pulse event and the detected second pulse event further comprises, if a (TOT) event occurs, approximating each of the level changes as an elapse of a threshold amount of time T ns.

Example 15 provides the method of example 6, wherein the reconstructing is performed using one of an arithmetic equation, a lookup table, a synchronous digital state machine or timers and an event-driven state machine.

Example 16 provides a method for amplitude correction in a photon counting computed tomography (PCCT) scanning system, the method including detecting a pulse at a pixel of the PCCT scanning system; for each change of voltage level detected in connection with the pulse, incrementing a counter; for each voltage level detected in connection with the pulse, determining whether an amount of time the pulse remains at the voltage level exceeds a threshold amount of time corresponding to a time-over-threshold (TOT) event; tracking the number of voltage level changes encountered between detection of the first pulse and detection of a second pulse; in response to a (TOT) event in connection with a voltage level, approximating the voltage level as a T ns time elapse; otherwise, approximating the voltage level change as a T/2 ns time elapse, where T is a threshold amount of time; and upon detection of the second pulse, using the approximated time elapse from the first pulse to compensate for contributions to the second pulse from the first pulse and resetting the counter to zero.

Example 17 provides the method of example 16, further comprising estimating an amplitude of the first pulse.

Example 18 provides the method of example 17, further comprising incrementing a counter corresponding to the estimated amplitude of the first pulse.

Example 19 provides the method of example 16, further comprising estimating an amplitude of the second pulse.

Example 20 provides the method of example 19, further comprising incrementing a counter corresponding to the estimated amplitude of the second pulse.

Example 21 provides a photon-counting computed tomography (PCCT) scanning system comprising a plurality of discriminators, wherein each discriminator is associated with a respective one of a plurality of threshold voltage levels; and counting circuitry configured to detect a first pulse event having a first detected level; detect a second pulse event having a second detected level; determine an amount of time that elapses between the detected first pulse event and the detected second pulse event; and reconstruct the first pulse and the second pulse using the first and second detected levels, the duration of time between the first and second pulse events, and a known pulse shape.

Example 22 provides the PCCT system of example 21, wherein the detecting the first pulse event is performed using one of a time-over-threshold (TOT) event detection technique and a tick-down event detection technique and wherein the detecting the second pulse event is performed using one of a time-over-threshold (TOT) event detection technique and a tick-down event technique.

Example 23 provides the PCCT system of example 21, wherein the counting circuitry is further configured to increment a first counter corresponding to the reconstructed first pulse; and increment a second counter corresponding to the reconstructed second pulse.

Example 24 provides the PCCT system of example 21, wherein the reconstructing comprises performing an amplitude correction technique on the first and second pulses.

Example 25 provides the PCCT system of example 21, wherein the counting circuitry comprises a synchronous circuit.

Example 26 provides the PCCT system of example 21, wherein the counting circuitry comprises an asynchronous circuit.

It should be noted that all of the specifications, dimensions, and relationships outlined herein (e.g., the number of elements, operations, steps, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, exemplary embodiments have been described with reference to particular component arrangements. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system may be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and may accommodate a large number of components, as well as more complicated/sophisticated arrangements and configurations. Accordingly, the examples provided should not limit the scope or inhibit the broad teachings of the electrical circuits as potentially applied to myriad other architectures.

It should also be noted that in this Specification, references to various features (e.g., elements, structures, modules, components, steps, operations, characteristics, etc.) included in "one embodiment", "exemplary embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It should also be noted that the functions related to circuit architectures illustrate only some of the possible circuit architecture functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Note that all optional features of the device and system described above may also be implemented with respect to the method or process described herein and specifics in the examples may be used anywhere in one or more embodiments.

The 'means for' in these instances (above) may include (but is not limited to) using any suitable component discussed herein, along with any suitable software, circuitry, hub, computer code, logic, algorithms, hardware, controller, interface, link, bus, communication pathway, etc.

Note that with the example provided above, as well as numerous other examples provided herein, interaction may be described in terms of two, three, or four network elements. However, this has been done for purposes of clarity and example only. In certain cases, it may be easier to describe one or more of the functionalities of a given set of flows by only referencing a limited number of network elements. It should be appreciated that topologies illustrated in and described with reference to the accompanying FIGURES (and their teachings) are readily scalable and may accommodate a large number of components, as well as more complicated/sophisticated arrangements and configurations. Accordingly, the examples provided should not limit the scope or inhibit the broad teachings of the illustrated topologies as potentially applied to myriad other architectures.

It is also important to note that the steps in the preceding flow diagrams illustrate only some of the possible signaling scenarios and patterns that may be executed by, or within, communication systems shown in the FIGURES. Some of these steps may be deleted or removed where appropriate, or these steps may be modified or changed considerably without departing from the scope of the present disclosure. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by communication systems shown in the FIGURES in that any suitable arrangements, chronologies, configurations, and timing mechanisms may be provided without departing from the teachings of the present disclosure.

Although the present disclosure has been described in detail with reference to particular arrangements and configurations, these example configurations and arrangements may be changed significantly without departing from the scope of the present disclosure. For example, although the present disclosure has been described with reference to particular communication exchanges, embodiments described herein may be applicable to other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 142 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A method of deconvolving overlapping pulses in a photon-counting computed tomography (CT) scanning system, the method comprising:

detecting, in a pixel of the photon-counting CT scanning system, a number of events in a sequence of discriminator codes corresponding to respective increasing voltage thresholds;

determining amounts of time that elapsed between successive ones of the detected events; and reconstructing a most likely sequence of events that caused a measured pattern of discriminator codes based on measured code values associated with each of the detected events, the amounts of time that elapsed between successive ones of the detected events, and a known basis pulse shape.

2. The method of claim 1, wherein the reconstructing is performed using an arithmetic equation.

3. The method of claim 1, wherein the reconstructing is performed using a lookup table.

4. The method of claim 1, wherein the reconstructing is performed using a synchronous digital state machine.

5. The method of claim 1, wherein the reconstructing is performed using timers and an event-driven state machine.

6. A method of deconvolving overlapping first pulse and second pulse in a photon-counting computed tomography (CT) scanning system, the method comprising:

detecting a first pulse event having a first detected level;
    detecting a second pulse event having a second detected level;
    determining an amount of time that elapsed between the detected first pulse event and the detected second pulse event; and
    reconstructing the first pulse and the second pulse using the first detected level and the second detected level, the amount of time that elapsed between the first pulse event and the second pulse event, and a known basis pulse shape.

7. The method of claim 6, wherein the detecting the first pulse event is performed using one of a time-over-threshold (TOT) event detection technique and a tick-down event detection technique.

8. The method of claim 6, wherein the detecting the second pulse event is performed using one of a time-over-threshold (TOT) event detection technique and a tick-down event technique.

9. The method of claim 6, further comprising incrementing a counter corresponding to the reconstructed first pulse.

10. The method of claim 6, further comprising incrementing a counter corresponding to the reconstructed second pulse.

11. The method of claim 6, wherein the reconstructing comprises performing an amplitude correction technique on the first pulse and second pulse.

12. The method of claim 6, wherein the determining an amount of time that elapsed between the detected first pulse event and the detected second pulse event comprises tracking a number of level changes that occur between the detection of the first pulse event and the detection of the second pulse event.

13. The method of claim 12, wherein the determining an amount of time that elapsed between the detected first pulse event and the detected second pulse event further comprises, if a time-over-threshold (TOT) event does not occur, approximating each of the level changes as an elapse of a threshold amount of time divided by two.

14. The method of claim 12, wherein the determining an amount of time that elapses between the detected first pulse event and the detected second pulse event further comprises, if a time-over-threshold (TOT) event occurs, approximating each of the level changes as an elapse of a threshold amount of time.

15. The method of claim 6, wherein the reconstructing is performed using one of an arithmetic equation, a lookup table, a synchronous digital state machine or timers and an event-driven state machine.

16. A method for amplitude correction in a photon-counting computed tomography (PCCT) scanning system, the method including:

detecting a pulse at a pixel of the PCCT scanning system;
    for each change of voltage level detected in connection with the pulse, incrementing a counter;
    for each voltage level detected in connection with the pulse, determining whether an amount of time the pulse remains at the voltage level exceeds a threshold amount of time corresponding to a time-over-threshold (TOT) event;
    tracking a number of voltage level changes encountered between detection of the pulse and detection of a second pulse at the pixel of the PCCT scanning system;
    in response to a TOT event in connection with a voltage level, approximating a voltage level change as a time elapse of the threshold amount of time; otherwise, approximating the voltage level change as a time elapse of half the threshold amount of time; and
    upon detection of the second pulse, using the approximated time elapse from the pulse to compensate for contributions to the second pulse from the pulse and resetting the counter to zero.

17. The method of claim 16, further comprising estimating an amplitude of the pulse.

18. The method of claim 17, further comprising incrementing a counter corresponding to the estimated amplitude of the pulse.

19. The method of claim 16, further comprising estimating an amplitude of the second pulse.

20. The method of claim 19, further comprising incrementing a counter corresponding to the estimated amplitude of the second pulse.

* * * * *